United States Patent [19]

McSpadden

[11] Patent Number: 5,035,617
[45] Date of Patent: Jul. 30, 1991

[54] ENDODONTIC INSTRUMENT

[76] Inventor: John T. McSpadden, 6918 Shallowford Rd., Chattanooga, Tenn. 37421

[21] Appl. No.: 534,153

[22] Filed: Jun. 5, 1990

[51] Int. Cl.$^5$ .......................... A61C 5/02; A61G 5/02
[52] U.S. Cl. ................................... 433/102; 433/164; 433/81
[58] Field of Search .......................... 433/81, 102, 164

[56] References Cited

U.S. PATENT DOCUMENTS

| | | | |
|---|---|---|---|
| 1,307,446 | 6/1919 | Kerr | 433/102 |
| 1,771,182 | 7/1930 | Lentulo | 433/164 |
| 1,969,808 | 8/1934 | Lentulo | 433/164 |
| 4,457,710 | 7/1984 | McSpadden | 433/164 |
| 4,538,989 | 9/1985 | Apairo, Jr. et al. | 433/102 |
| 4,634,378 | 1/1987 | Leonard | 433/102 |
| 4,871,312 | 10/1989 | Heath | 433/102 |
| 4,904,185 | 2/1990 | McSpadden | 433/102 |

*Primary Examiner*—John J. Wilson

[57] ABSTRACT

An endodontic instrument having a rotatable shank and a working portion which extends along at least a portion of the length of the shank to a tip includes two continuous helical flutes which spiral along the length of the working portion. Each of the helical flutes has a shoulder which generally faces in the same direction along the length of the working portion as the shoulder of the other flute and which has a helical angle which is different from the helical angle of the shoulder of the other flute. In one embodiment, the instrument includes shoulders which generally face in the direction along the working portion toward the tip and is well-suited for thermomechanically condensing gutta-percha in a root canal of a tooth and for cutting dentinal chips from the wall of an extirpated root canal and transporting the cut chips to the terminus of the root canal system. In another embodiment, the instrument includes shoulders which generally face in the direction along the working portion away from the tip and is well-suited for extirpating a root canal as the working portion is either rotated or moved in inserting-withdrawal motions within the canal.

8 Claims, 2 Drawing Sheets

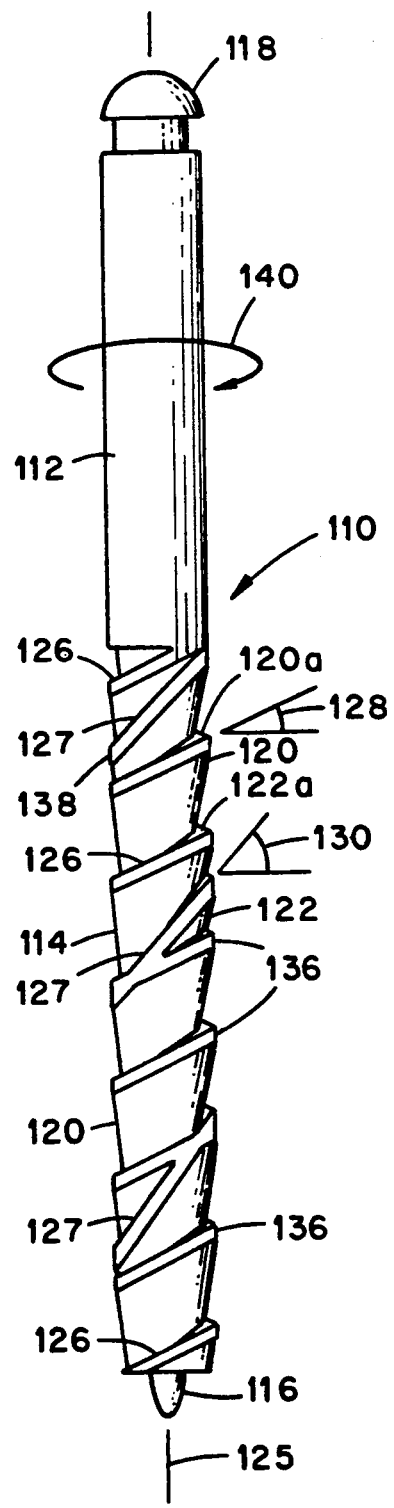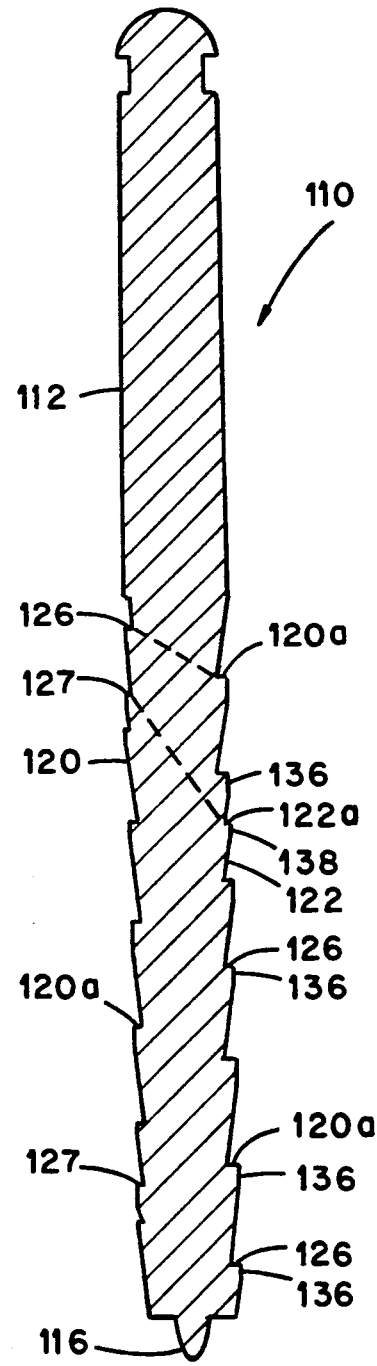

ENDODONTIC INSTRUMENT

The present invention relates generally to the field of endodontics and relates more particularly to instruments used for enlarging and obturating an extirpated root canal.

One of the more technically difficult and delicate procedures in the field of dentistry is that of obturating (filling) an extirpated (stripped) tooth root canal system. During an obturating procedure, the extirpated root canal must be filled with a filler material in a homogeneous three-dimensional manner without voids in order to prevent any leakage or communication between the root canal and the surrounding and supporting tissues of the tooth. The difficulty is further compounded by the possibility of breakage of the compactor instrument used to compact filler material within the canal, concern of extrusion of the filler material through the apical foramen of the tooth root and eventual shrinkage of the filler material if introduced into the canal in a heated condition.

In the typical or traditional method of obturating a tooth root canal, strand-like pieces of gutta-percha or some other thermoplastic material in the form known as points or cones, are inserted into the extirpated root canal. These gutta-percha points are physically compacted, or condensed, by small instruments known as "plungers", "spreaders" or "heat carriers". These instruments are heated and manipulated into contact with the gutta-percha points positioned within the root canal to soften and compact the points within the canal. Normally, the gutta-percha must be compacted or condensed within the canal in both vertical and horizonal directions to suitably fill the canal. However, this procedure is time-consuming and, unless the endodontist is highly skilled, the results are not always satisfactory.

Another method of obturating a canal involves heating the gutta-percha before it is inserted into the canal and then injecting it into the canal while it is in a plastic state. The difficulty with this method relates to the possibility that the plasticized gutta-percha may extrude through the apical foramen and into the self-supporting tissues of the root structure.

Still another obturating method, such as is described in U.S. Pat. No. 4,758,156, involves application of a heated thermoplastic material, such as gutta-percha, on a carrier shaft of filler material and the insertion of the carrier shaft into the root canal. The carrier shaft, having a handle portion and a distal portion, is then held stationary and the handle portion is severed from the distal portion leaving only the distal portion within the canal. A limitation associated with this method is that the filler material cannot be manipulated, i.e., worked with a rotatable instrument, once positioned within the canal. Because of the inability to work this filler material with a rotatable instrument, enlargements frequently associated with the canal such as may include areas of internal resorption, auxiliary canals, webs and fins or the length of a lengthy root canal system may prevent the carrier shaft from being insufficiently encapsulated when the terminus of the canal is reached.

Further obturating methods, such as those described in U.S. Pat. Nos. 4,353,698, 4,457,710 and 4,904,185, involve the use of a mechanically driven, multi-fluted, rotatable instrument for simultaneously plasticizing, introducing and condensing gutta-percha within a canal. To use this type of instrument, the instrument is rapidly rotated within the canal and manipulated into contact with gutta-percha fed to the canal. While gutta-percha can normally be condensed in a satisfactory manner within the canal with this type of instrument, there is always a concern that if sufficient vertical components of force are exerted by the instrument upon the gutta-percha for vertical condensation, then the lateral components of force exerted by the instrument may be inadequate for horizontal condensation. Similarly, if sufficient lateral components of force are exerted by the instrument upon the gutta-percha for horizontal condensation, then the vertical components of force exerted by the instrument may be inadequate for vertical condensation. This concern is of particular interest when manipulating low-fusing gutta-percha which normally requires very little heat to plasticize and a relatively slow rotation of the instrument to manipulate.

Another difficulty associated with the obturating of an extirpated tooth root canal system is the providing of the apical portion (root tip) of the tooth root canal system with an apical seal which provides a biocompatible environment conducive for healing. Such an environment may be provided by packing dentinal chips within the apical portion of the root canal system. Heretofore, dentinal chips have been removed from the wall of a root canal with conventional hand instruments, files and reamers and subsequently packed within the apical portion with hand pluggers in a slow and difficult process.

Another difficult technique or process is that of extirpating or enlarging the root canal system with instruments known as reamers and files. Reamers commonly include cutting edges which run more parallel, rather than perpendicular, to the longitudinal axis of the instrument and are used by rotating the instrument so that its cutting edges ream the canal system. Files, on the other hand, commonly include cutting edges which run more perpendicular, rather than parallel, to the longitudinal axis of the instrument and are used by inserting and withdrawing the instrument, e.g., reciprocating the instrument, into and out of the canal in an alternating fashion to file the canal system. Known reamers and files are limited, however, in that reamers cannot be moved in insertion-withdraw motions within a canal and files cannot be rotated within a canal without compromising the cutting effectiveness of the instruments.

Accordingly, it is an object of the present invention to provide an endodontic instrument for condensing gutta-percha within a root canal by rotating the instrument into contact with gutta-percha fed to the canal and for providing vertical and lateral components of force adequate for condensing the gutta-percha vertically and horizontally.

Another object of the present invention is to provide such an instrument which is well-suited for cutting dentinal chips from the wall of an extirpated root canal and transporting the cut chips to the apical portion of the canal system for purposes of packing the apical portion of the tooth root with the chips.

Still another object of the present invention is to provide an endodontic instrument for enlarging a root canal as the instrument is rotated and/or moved in an insertion-withdrawal motion within the canal wherein the effectiveness of one of the rotary motion and the insertion-withdrawal motion is not compromised by other of the insertion-withdrawal and rotary motion of the instrument.

More particularly, the invention is provided by an endodontic instrument for use during obturation or extirpation of a root canal having a shank and a working portion extending along at least a portion of the length of the shank and terminating at a tip end. Flute means are formed in the working portion so as to define two continuous helical flutes which spiral along the length of the working portion. Each of the helical flutes has a shoulder which generally faces in the same direction along the length of the working portion as the shoulder of the other flute and which has a helical angle which is different from the helical angle of the shoulder of the other flute.

In one embodiment of the instrument, the shoulders generally face in the direction along the working portion toward the tip end. By rotating the instrument working portion into contact with gutta-percha introduced into a root canal, the filler material is urged by the shoulders in different directions relative to the longitudinal axis of the shank. For example, the filler material may be principally urged toward the tip end of the working portion by the shoulder oriented more perpendicular to the longitudinal axis of the shank while the filler material may be principally urged radially outwardly of the working portion by the shoulder oriented more parallel to the longitudinal axis of the shank. The rotation of the instrument working portion in contact with the wall of an extirpated root canal effects a cutting of dentinal chips from the canal wall by the shoulder oriented more parallel to the longitudinal axis of the shank and a transporting of the cut chips toward the terminus of the root canal by the shoulder oriented more perpendicular to the longitudinal axis of the shank.

In another embodiment of the instrument, the shoulders generally face in the direction along the working portion away from the tip end. By rotating the instrument working portion in contact with the wall of a root canal, the shoulder oriented more parallel to the longitudinal axis of the shank principally reams the wall surface, and by moving the working portion in contact with the root canal wall with insertion-withdrawal motions, the shoulder oriented more perpendicular to the longitudinal axis of the instrument principally files the wall surface.

A more complete understanding of the present invention will be had by reference to the specification and accompanying drawings wherein like numerals refer to like parts throughout.

FIG. 3 is a diagrammatic side view of another embodiment of an endodontic instrument embodying various features of the present invention; and FIG. 4 is a longitudinal cross-sectional view of the instrument of FIG. 3.

Figure 1:
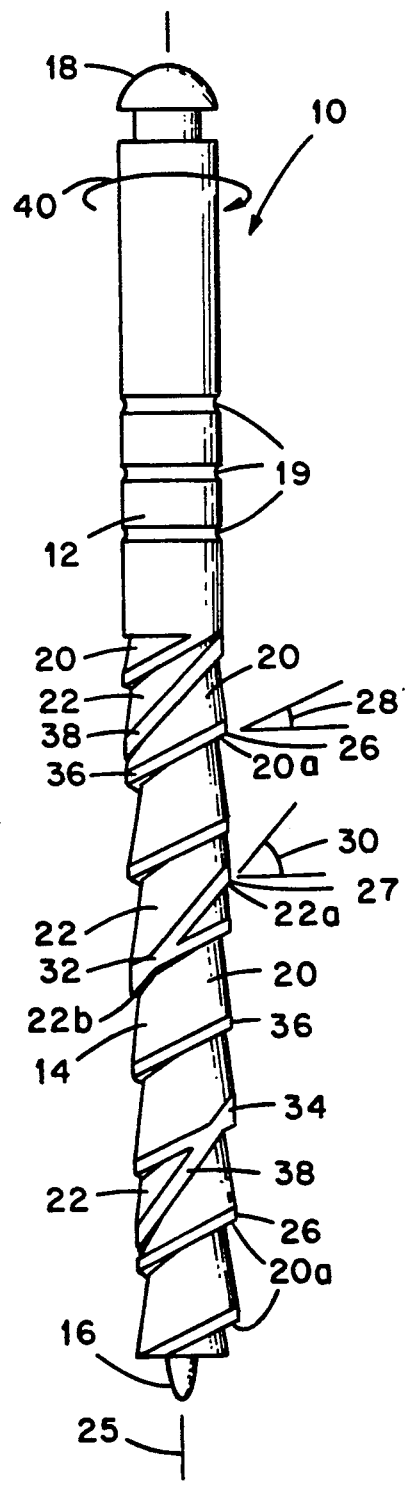
FIG. 1 is a diagrammatic side view of an embodiment of an endodontic instrument embodying various features of the present invention.
Figure 2:
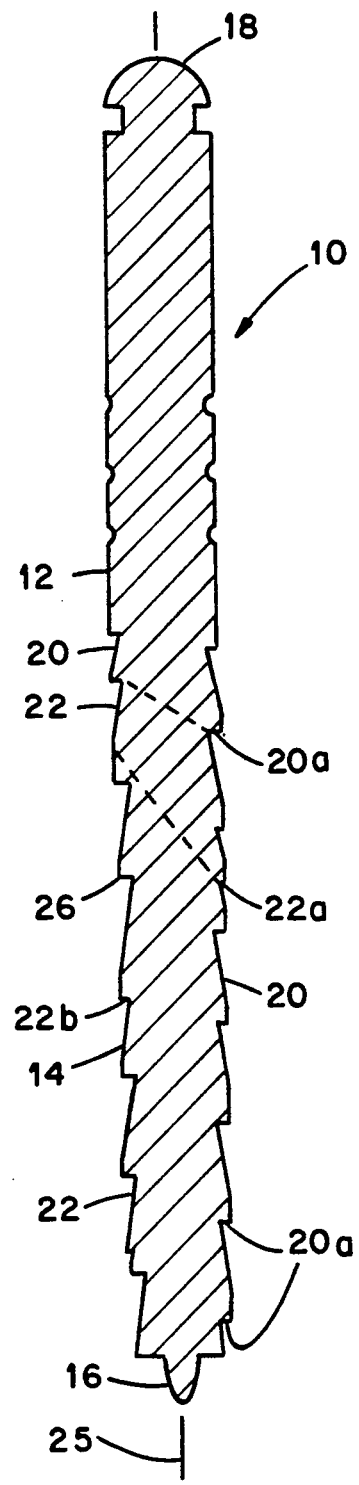
FIG. 2 is a longitudinal cross-sectional view of the instrument of FIG. 1.

With reference to FIGS. 1 and 2, there is shown a condenser instrument, generally denoted as 10, having a shank 12 with a working portion 14 extending along a portion of the shank length. The working portion 14 is illustrated as being substantially cylindrical in form and is provided with a fitting 18 adjacent its upper end which is adapted to mate with the chuck of a dental handpiece (not shown) or with a handle (not shown) for use of the instrument 10 by hand. In addition, the shank 12 is provided with a tip 16 adjacent the end of the working portion 14 opposite the fitting 18 and indicia for providing an indication of the depth of penetration of the instrument 10 into the root canal. In the depicted instrument 10, these depth-indicating indicia are in the form of spaced rings 19 formed in the shank 12.

The working portion 14 of the instrument 10 includes flute means in the form of two helical flutes 20, 22 which spiral along the length of the working portion 14 between the working portion ends. Each flute 20 or 22 includes a generally downwardly-directed shoulder 20a or 22a which extends generally radially outwardly from the longitudinal axis 25 of the shank 12 to a peripheral edge 26 or 27 and which generally faces toward the tip end 16 of the shank 12. When used to condense gutta-percha within a root canal, the instrument 10 is intended to be rotated in the direction of the arrow 40 in FIG. 1. Accordingly, each helical flute 20 or 22 follows a right-hand twist pattern from the upper end of the working portion 14 to the tip end 16. However, in accordance with the broader aspects of this invention, each helical flute 22 or 20 may follow a left-hand twist pattern between the working portion ends if it is desired to rotate the instrument 10 in the rotational direction opposite the direction of the arrow 40.

It is a feature of the instrument 10 that the shoulders 20a and 22a possess helical angles 28 and 30, respectively, which are different from one another. Consequently, one shoulder 22 is oriented more parallel to the longitudinal axis 25 of the shank 12 while the other shoulder 20a is oriented more perpendicular to the longitudinal axis 25 of the shank 12. In addition, and as best illustrated in FIG. 1, each flute 20 or 22 is interrupted by the other flute 22 or 20 as it spirals along the length of the working portion 14. In the depicted instrument 10, flute 20 is interrupted by flute 22 at no fewer than two locations indicated in FIG. 1 as 32 and 34.

In order to preserve the constancy of diameter at the periphery of the working portion 14, it is preferred that the working portion 14 be provided with a peripheral land 36 or 38 adjacent a corresponding one of the helical shoulders 20a or 22a. Each land 36 or 38 provides a spiral or helical surface which faces radially outwardly of the working portion 14 at the periphery thereof and meets its corresponding shoulder 20a or 22a at the peripheral edge 26 or 27. The rake angle of the edges 26, 27 may be positive, negative or neutral.

Prior to utilization of the instrument 10 during an obturating procedure, a tooth root canal is extirpated, cleaned and shaped to provide adequate access. Gutta-percha is then introduced into the root canal either as a coating applied about a compactor shaft in a plasticized state, by injection of the gutta-percha into the canal in a plasticized state, by inserting gutta-percha cones or points into the canal or by a combination of the aforementioned introduction methods. The shank 12 and, more particularly, the working portion 14 is then inserted into the root canal and rotated into contact with the gutta-percha. If the gutta-percha is introduced into the canal as a point or cone, the shank rotation may cause plastification of the gutta-percha by frictional heat.

In any event, the plasticized gutta-percha which has been either plasticized by frictional heat or by extraneous means such as by heating or the use of a solvent, is urged by the shoulders 20a and 22a in different directions. In the depicted instrument 10, gutta-percha is principally forced radially outwardly by the shoulder 22a of the rotating working portion 14 and principally forced downwardly toward the tip end 16 by the shoulder 20a of the rotating working portion 14. Accordingly, the helical angles 28 and 30 are appropriately sized to effect the radially-outward urging and/or downward urging of the gutta-percha as desired. By way of example, the helical angle 30 of shoulder 22a may be within the range from about thirty to fifty degrees for principally urging gutta-percha radially outwardly, and the helical angle 28 of shoulder 20a may be within the range from about fifteen to thirty degrees for principally urging gutta-percha downwardly toward the tip end 16.

It follows that as the plasticized gutta-percha is urged both radially outwardly and toward the tip end 16 of the shank 12 by the shoulders 20a and 22a, the gutta-percha is effectively compacted and condensed within the canal system in both vertical and horizontal directions. Consequently, the canal and any voids associated therewith may be quickly and satisfactorily filled by using the instrument 10 with no need that the endodontist possess as high a degree of skill as would otherwise be needed with conventional instruments.

In the case of gutta-percha which has been plasticized by extraneous heat or by solvent when introduced into the root canal system, the rotation of the instrument 10 may be effected manually. If, on the other hand, the gutta-percha introduced into the canal must be plasticized by frictional heat, it may be desired to rotate the instrument 10 with a low speed handpiece. If desired, the condenser instrument 10 may be withdrawn while rotating to fill any voids in the root canal system or the rotation of the shank 12 may be stopped and the shank 12 left in the root canal to prevent shrinkage and to inform the endodontist of the appropriate depth of condensation of the gutta-percha. Thus, the instrument 10 provides the endodontist with means for providing a more effective seal of the root canal system and more alternatives and control in manipulating the gutta-percha into place in the root canal system than that provided by previously known condenser instruments.

The instrument 10 is also well-suited for providing the apical portion (root tip) of a root canal system with a seal which provides a biocompatible environment conducive for healing. To this end, the instrument working portion 14 is rotated the direction of arrow 40 in contact with the wall of an extirpated root canal so that the peripheral edges 26, 27 move generally along the surface of the wall. As the working portion 14 is rotated, the peripheral edge 27 associated with the shoulder 22a cuts dentinal chips from the root canal wall while the peripheral edge 26 associated with the shoulder 20a transports the cut chips downwardly toward the tip end 16. Thus, the helical shoulder 22a oriented more parallel to the longitudinal axis 25 of the shank 12 effects the removal of the dentinal chips and the helical shoulder 20a oriented more perpendicular to the longitudinal axis 25 effects the transference of the dentinal chips toward the terminus of the canal system so that a biocompatible apical plug is provided in the apical portion of the canal system. In addition, the possibility of apical extrusion of the gutta-percha subsequently introduced into the canal is reduced by the provision of the apical plug.

With reference to FIGS. 3 and 4, there is shown an enlargement instrument, generally denoted 110, for the extirpation, cleaning and enlarging of a root canal system. The enlargement instrument 110 has a shank 112 with a working portion 114 extending along at least a portion of the shank length. The working portion 114 is illustrated as being substantially cylindrical in form and is provided with a fitting 118 adjacent its upper end which is adapted to mate with the chuck of a dental handpiece (not shown) or is provided with a handle (not shown) for manual use. In addition, the shank 112 is provided with a tip end 116 opposite the fitting 118.

The working portion 114 of the instrument 110 includes flute means in the form of two helical flutes 120, 122 which spiral along the length of the working portion 114. Each flute 120 or 122 is provided with a shoulder 120a or 122a which extends generally radially outwardly from the longitudinal axis 125 of the shank 112 to a peripheral edge 126 or 127 and which generally faces upwardly toward the fitting 118. When used to extirpate a root canal, the instrument 110 is intended to be rotated in the direction of the arrow 140 in FIG. 3. Accordingly, each helical flute 120 or 122 follows a right-handed twist from the upper end of the working portion 114 to the tip end 116.

It is a feature of the instrument 110 that the shoulders 120a and 122a possess helical angles 128 and 130, respectively, which are different from one another. Consequently, the shoulder 120a is oriented more perpendicular the longitudinal axis 125 of the instrument shank 112 than is the shoulder 122a. By comparison, the shoulder 122a is oriented more parallel to the longitudinal axis 125 of the instrument shank 112 than is the shoulder 120a.

To ensure that the outermost diameter of the helical shoulders 120a and 122a are of equal distance from the longitudinal axis 125 of the instrument 110, the working portion 114 may be provided with a peripheral land 136 or 138 adjacent a corresponding shoulder 120a or 122a. Each land 136 or 138 provides a spiral or helical surface which faces radially outwardly of the working portion 114 at the periphery thereof and meets its corresponding shoulder 120a or 122a at the peripheral edge 126 or 127.

To use the instrument 110 to enlarge and shape a root canal, the instrument 110 is both rotated and moved in insertion-withdrawal, e.g., reciprocation, motions within a canal. As the instrument 110 is rotated, the cutting shoulder 122a running more parallel to the longitudinal axis of the instrument 110 is effective to ream the root canal surface. The cutting shoulder 120a running more perpendicular to the longitudinal axis of the instrument 110 is most effective during the filing motion of canal preparation. Both shoulders 120a and 122a remove debris from the canal system and urge the debris cut from the canal wall toward the fitting 118 of the shank 112.

Traditionally, canal preparation has been effected by a technique known as the "quarter turn withdrawal" process of inserting an instrument having the approximate diameter of the canal into the root canal, applying pressure toward the terminus of the canal and rotating the instrument one-quarter turn and withdrawing the instrument. In this technique, a file might be used to ream or a reamer might be used to file, but the cutting shoulders of the file or reamer may possess a helical angle somewhere between the ideal filing helical angle and the ideal reaming helical angle resulting in a compromise in effectiveness of reaming and filing motions when attempting to perform both motions with the same instrument. With the present invention, a cutting shoulder having a helical angle more suitable for filing and a cutting shoulder having a helical angle more suitable for reaming can be simultaneously embodied in the same instrument previously unavailable in root canal instruments. By way of example, the helical angle 128 of shoulder 120 may be within the range from about fifteen to thirty degrees for best removing debris from the canal wall with filing motions, and the helical angle 130 of shoulder 122a may be within the range from about thirty to fifty degrees for best removing canal wall debris with reaming motions.

The foregoing detailed description is given primarily for clearness of understanding and no unnecessary limitations are to be understood therefrom for modifications will become obvious to those skilled in the art on reading this disclosure and may be made without departing from the spirit of the invention and scope of the appended claims. For example, although the aforedescribed embodiments 10 and 110 have each been described as including only two shoulders, an instrument in accordance with the broader aspects of this invention may include more than two shoulders as long as at least one of the shoulders possesses a helical angle which is different from that of the remaining shoulders.

I claim:

1. An endodontic instrument for use during obturation or extirpation of a root canal comprising:
    a shank;
    a working portion extending along at least a portion of the length of the shank and terminating at a tip end; and
    flute means formed in said working portion defining two continuous helical flutes which spiral along the length of the working portion, each of said helical flutes having a shoulder which generally faces in the same direction along the length of the working portion as does the shoulder of the other flute and which has a helical angle which is different from the helical angle of the shoulder of the other flute.

2. The instrument as defined in claim 1 wherein the working portion terminates at a tip end and the shoulders generally face in the direction along the working portion toward the tip end.

3. The instrument as defined in claim 2 wherein the helical angles of the shoulders are sized so that rotation of the instrument in contact with filler material used to obturate a canal is principally urged toward the tip end of the working portion by one of said shoulders and is principally urged radially outwardly of the working portion by the other of said shoulders.

4. The instrument as defined in claim 2 wherein the helical angle of the shoulder of one of the helical flutes is within the range from about thirty to fifty degrees and the helical angle of the shoulder of the other of the helical flutes is within the range from about fifteen to thirty degrees.

5. The instrument as defined in claim 2 wherein each shoulder terminates a relatively sharp edge at the periphery of the working portion so that rotation of the instrument in contact with the wall of an extirpated root canal effects a cutting by one of the shoulders of dentinal chips from the wall thereof and a transporting by the other of the shoulders of the cut chips toward the terminus of the root canal.

6. The instrument as defined in claim 1 wherein the working portion terminates at a tip end and the shoulders generally face in the direction along the working portion away from the tip end.

7. The instrument as defined in claim 6 wherein the helical angle of the shoulder of one of the helical flutes is within the range from about thirty to fifty degrees and the helical angle of the shoulder of the other of the helical flutes is within the range from about fifteen to thirty degrees.

8. The instrument as defined in claim 6 wherein the helical angles of the shoulders are sized so that as the working portion is rotated in contact with the wall of a root canal, one of the shoulders principally reams the wall and so that as the working portion is moved in contact with the wall of a root canal with insertion-withdrawal motions, the other of the shoulders principally files the wall.

* * * * *